(12) United States Patent
Fontanazzi et al.

(10) Patent No.: US 11,020,518 B2
(45) Date of Patent: *Jun. 1, 2021

(54) APPARATUS AND A METHOD FOR EXTRACORPOREAL BLOOD TREATMENT

(71) Applicant: GAMBRO LUNDIA AB, Lund (SE)

(72) Inventors: Francesco Fontanazzi, Modena (IT); Francesco Paolini, Ganaceto (IT); Fabio Grandi, Forli (IT)

(73) Assignee: Gambro Lundia AB, Lund (SE)

( * ) Notice: Subject to any disclaimer, the term of this patent is extended or adjusted under 35 U.S.C. 154(b) by 411 days.

This patent is subject to a terminal disclaimer.

(21) Appl. No.: 16/160,276

(22) Filed: Oct. 15, 2018

(65) Prior Publication Data
US 2019/0046711 A1    Feb. 14, 2019

Related U.S. Application Data

(63) Continuation of application No. 14/429,435, filed as application No. PCT/IB2013/058671 on Sep. 19, 2013, now Pat. No. 10,130,744.
(Continued)

(30) Foreign Application Priority Data

Sep. 21, 2012  (EP) .................................. 12006622

(51) Int. Cl.
*A61M 1/16*    (2006.01)
*A61M 1/34*    (2006.01)
*A61M 1/36*    (2006.01)

(52) U.S. Cl.
CPC ............ *A61M 1/1611* (2014.02); *A61M 1/34* (2013.01); *A61M 1/3403* (2014.02);
(Continued)

(58) Field of Classification Search
CPC .... A61M 1/1611; A61M 1/34; A61M 1/3403; A61M 1/3413; A61M 1/3434;
(Continued)

(56) References Cited

U.S. PATENT DOCUMENTS 4,324,663 A    4/1982  Hirel
4,469,593 A    9/1984  Ishihara
(Continued)

FOREIGN PATENT DOCUMENTS

CA    1121738    4/1982
CN    1678360    10/2005
(Continued)

OTHER PUBLICATIONS

Casagrande et al., "A New Method to Evaluate Patient Characteristic Response to Ultrafiltration During Hemodialysis," *The International Journal of Artificial Organs*, vol. 30, No. 5, 2007, pp. 1-8.
(Continued)

*Primary Examiner* — Kai H Weng
(74) *Attorney, Agent, or Firm* — Mueting Raasch Group

(57) ABSTRACT

An apparatus for extracorporeal blood treatment comprises a sensor (10) for emitting a signal indicating a variation in blood volume (ΔBv") of an individual (7) subjected to extracorporeal blood treatment and a sensor (14) for emitting a signal indicating a weight loss of the individual. A control unit (20) receives the signals, compares the ratio between the relative variation of blood volume (ΔBv/BV) and the relative variation of weight loss (AWL/TW) of the individual with a desired value, and controls the weight loss of the individual on the basis of the comparison. The apparatus enables automatically controlling a dialysis, preventing some complications due to hypotension.

26 Claims, 2 Drawing Sheets

Related U.S. Application Data

(60) Provisional application No. 61/703,898, filed on Sep. 21, 2012.

(52) U.S. Cl.
CPC ........ *A61M 1/3413* (2013.01); *A61M 1/3434* (2014.02); *A61M 1/3437* (2014.02); *A61M 1/3441* (2013.01); *A61M 1/3607* (2014.02); *A61M 1/3609* (2014.02); *A61M 1/3687* (2013.01); *A61M 2205/3306* (2013.01); *A61M 2205/3331* (2013.01); *A61M 2205/50* (2013.01); *A61M 2205/502* (2013.01); *A61M 2205/505* (2013.01)

(58) Field of Classification Search
CPC .............. A61M 1/3437; A61M 1/3441; A61M 1/3607; A61M 1/3609; A61M 1/3687; A61M 2205/3306; A61M 2205/3331; A61M 2205/50; A61M 2205/502; A61M 2205/505

See application file for complete search history.

(56) References Cited

U.S. PATENT DOCUMENTS

| | | | |
|---|---|---|---|
| 4,629,015 | A | 12/1986 | Fried |
| 5,230,341 | A | 7/1993 | Polaschegg |
| 5,938,938 | A | 8/1999 | Bosetto |
| 7,131,956 | B1 | 11/2006 | Pirazzoli |
| 8,075,509 | B2 | 12/2011 | Molducci |
| 8,496,807 | B2 | 7/2013 | Mori |
| 8,512,564 | B2 | 8/2013 | Bene |
| 8,741,147 | B2 | 6/2014 | Bene |
| 8,881,600 | B2 | 11/2014 | Puppini |
| 2002/0068015 | A1 | 6/2002 | Polaschegg |
| 2010/0219129 | A1 | 9/2010 | Bene |
| 2011/0118647 | A1 | 5/2011 | Paollini |
| 2011/0201989 | A1 | 8/2011 | Holmer |
| 2015/0033829 | A1 | 2/2015 | Puppini |

FOREIGN PATENT DOCUMENTS

| | | |
|---|---|---|
| CN | 101232910 | 12/2011 |
| CN | 102186513 | 8/2014 |
| EP | 0186973 | 7/1986 |
| EP | 0358873 | 3/1990 |
| EP | 0516152 | 12/1992 |
| EP | 1872811 | 1/2008 |
| GB | 2052303 | 1/1981 |
| IT | 1105139 | 10/1985 |
| IT | 1252601 | 1/1996 |
| IT | 1276468 | 6/1997 |
| WO | WO 93/00938 | 1/1993 |
| WO | WO 97/02057 | 1/1997 |
| WO | WO 2010/004400 | 1/2010 |

OTHER PUBLICATIONS

Dialysis from Wikipedia, http://de.wikipedia.org/wiki/Dialyse. English translation enclosed.
Lamberti et al., "A Digital Computer Model for Optical Programming of Hemodialytic Treatment," *The International Journal of Artificial Organs*, vol. 11, No. 4, 1988, pp. 235-242.
Santoro et al., "Blood Volume Regulation During Hemodialysis," *American Journal of Kidney Diseases*, vol. 32, No. 5, 1998, pp. 739-748.
Schönweiß, "Dialysis Primer 3, Individualism, Flexibility and Quality in Dialysis," *abakiss Verglasgesellschaft mbH*, vol. 2. English translation included.
Schroeder et al., "Continuous Haematocrit Monitoring During Intradialytic Hypotension: Precipitous Decline in Plasma Refill Rates," *Nephrology Dialysis Transplantation*, No. 19, 2004, pp. 652-656.
Von Sarti et al., "Optical Hemodialysis Programming by a Mathematical Modell," 10th Annual Conference of the IEEE EMBS, 1988.
Winkler et al., "Blood Volume Monitoring," *Contrib Nephrol. Basel*, vol. 161, 2008 pp. 119-124.

APPARATUS AND A METHOD FOR EXTRACORPOREAL BLOOD TREATMENT

This application is a continuation of U.S. patent application Ser. No. 14/429,435, filed Mar. 19, 2015 and which is a U.S. National Stage Application of International Application No. PCT/IB2013/058671, filed Sep. 19, 2013, which was published in English on Mar. 27, 2014 as International Patent Publication WO 2014/045224 A1, which claims the benefit under 35 U.S.C. 119(e) of U.S. Provisional Application No. 61/703,898 filed Sep. 21, 2012. International Application No. PCT/IB2013/058671 also claims priority to European Application No. 12006622.0 filed Sep. 21, 2012.

FIELD OF THE INVENTION

The present invention relates to an apparatus for extracorporeal blood treatment.

Specifically, though not exclusively, the invention can be usefully applied for treatment of kidney failure.

BACKGROUND OF THE INVENTION

Automatic control of a dialysis treatment is known, by controlling a flow rate of weight loss in the patient and the conductivity of the dialysis fluid, while taking into account the real-time physiological response of the patient to the treatment, in particular by monitoring the variation of the blood volume of the patient, with the purpose of improving the patient's well-being and in general preventing any eventual hypotensive phenomena during the treatment.

Italian patent IT 1252601 describes an automatic system in which desired and time-variable values relating to relative variable blood volumes are stored; the values of some patient parameters are then calculated (corresponding to the coefficients of a predetermined mathematic model having in input one or more machine dimensions and in output the relative variation of blood volume) as a function of the real response of the patient to the treatment; then the machine dimensions are calculated (the weight loss velocity and the osmolarity of the dialysis solution) as a function of the calculated patient parameters. Italian patent IT 1276468 discloses a system in which desired values and real values of the relative variation in blood volume and patient weight loss are acquired; the real values of the weight loss velocity and the conductivity of the dialysis liquid are acquired during treatment, permitted values are also stored as a function of the time, the relative variation of blood volume, accumulated weight loss, velocity of weight loss and conductivity of the dialysis liquid; lastly, the operative values of the velocity of the weight loss and the conductivity of the dialysis liquid are calculated.

An article entitled "A new method to evacuate patient characteristic response to ultrafiltration during hemodialysis", published in "The International Journal of Artificial Organs", Vol. 30, no. 5, 2007, teaches that the parameter known as "Plasma Refilling Index" (PRI), defined by the ratio between the total body water of an individual and the blood volume, provides useful indications for the comprehension of the response of a patient subjected to dialysis, in particular his or her behaviour in relation to the operation of vascular "refilling", i.e. the quantity of liquid which is displaced from the interstitial space of the patient's body to the intravascular space.

Finally, patent EP 2293829 teaches setting, in the machine, an optimal patient refilling index value, and also providing the weight value of the patient. During machine setting, input of a total weight loss value is also required.

The percentage variation of the blood volume to be obtained at the end of treatment is therefore calculated on the basis of the percentage weight loss and the preset value of the refilling index.

Starting from this desired value of percentage variation of the blood volume at end of treatment, a desired profile of the variation is calculated starting from a nil initial value.

SUMMARY

An aim of the present invention is to provide an automatic control system of an extracorporeal blood treatment able to effectively adapt to the various characteristics and needs of each patient in order to guarantee maximum well-being during treatment.

An objective of the invention is to provide a control system that is able to prevent some complications during the course of the treatment, such as for example collapses, cramps, vomiting, headaches and so on.

A further aim is to make available a control system that can be set by an operator simply, rapidly and reliably.

A still further aim is to provide a control system that takes account with particular precision of the effective physiological situation of the patient and which can therefore be adapted very effectively to the individual reactions of the patient during the course of treatment.

At least one of the above-indicated aims is substantially attained by a blood treatment apparatus according to one or more of the accompanying claims. Aspects of the invention are illustrated in the following.

In a 1st independent aspect of the invention, an extracorporeal blood treatment apparatus, comprises: a blood treatment device (2) having a blood chamber (3) and a fluid chamber (4) separated from one another by a semipermeable membrane (5); an extracorporeal blood circuit (6) connected to the blood chamber such as to transport blood from an individual (7) to the blood chamber (3) and to return the blood from the blood chamber to the individual; a sensor (10) predisposed in the extracorporeal blood circuit (6) for emitting at least a signal indicating the variation of blood volume ($\Delta BV$) of the individual (7) subjected to the extracorporeal blood treatment; a sensor (14) configured such as to emit at least a signal indicating the weight loss of the individual (7) subjected to the extracorporeal blood treatment; a weight loss system for actuating the weight loss of the individual during the extracorporeal blood treatment; a control unit (20) configured for performing following operations: receiving the signals indicating a variation of blood volume ($\Delta BV$) and weight loss during the extracorporeal blood treatment; acquiring a desired value ($IR_{des}$) of a parameter of the individual; determining a calculated value (IR) of the parameter of the individual according to the variation in hematic volume ($\Delta BV$) and a variation in weight loss ($\Delta WL$) of the individual; optionally verifying whether the relation between the relative variation of blood volume ($\Delta BV/BV$) and the relative variation in weight loss ($\Delta WL/TW$) of the individual is in a predetermined relation with a desired value ($IR_{des}$; $K_{des}$); controlling, the weight loss system on a basis of a desired value ($_{IRdes}$; $K_{des}$) of the parameter of the individual and the calculated value (IR;K) of the parameter of the individual, or on the basis of the verification.

A 2nd independent aspect of the invention comprises a control method of an apparatus for extracorporeal blood treatment, the apparatus comprising: a blood treatment device (2) having a blood chamber (3) and a fluid chamber (4) separated from one another by a semipermeable membrane (5); an extracorporeal blood circuit (6) connected to the blood chamber so as to transport blood from an individual (7) to the blood chamber (3) and to return the blood from the blood chamber to the individual; a sensor (10) predisposed in the extracorporeal blood circuit (6) for emitting at least a signal indicating the variation of blood volume (ΔBV) of the individual (7) subjected to the extracorporeal blood treatment; a sensor (14) configured such as to emit at least a signal indicating the weight loss of the individual (7) subjected to the extracorporeal blood treatment; a Weight loss system for actuating the weight loss of the individual during the extracorporeal blood treatment; the method including performing a control process comprising: receiving the signals indicating a variation of blood volume (ΔBV) and weight loss during the extracorporeal blood treatment; acquiring a desired value ($IR_{des}$) of a parameter of the individual; determining a calculated value (IR) of the parameter of the individual according to the variation in hematic volume (ΔBV) and a variation of weight loss (ΔWL) of the individual; optionally verifying whether the ratio between the relative variation of blood volume (ΔBV/BV) and the variation in weight loss (ΔWL/TW) of the individual is in a predetermined relation with a desired value ($IR_{des}$;$K_{des}$); controlling the weight loss system on a basis of the desired value ($IR_{des}$;$K_{des}$) of the parameter of the individual and the calculated value (IR;K) of the parameter of the individual or on the basis of the verification. In a 3rd aspect according to any one of the preceding aspects the control process (or the control unit) performs the operations of receiving the verification and control signals iteratingly during the treatment, in detail for a plurality of times.

In a 4th aspect according to any one of the preceding aspects, the control process (or the control unit) receives a weight value of the individual and determines the desired value ($IR_{des}$) on a basis of the weight value.

In a 5th aspect according to the preceding aspect, the control process (or the control unit) receives at least an optimal value of a parameter of the individual (IR) and determines the desired value (IRdes) on a basis of the weight value and the optimal value.

In a 6th aspect according to any one of the preceding aspects, the parameter of the individual (IR) comprises an index which is a function of the ability of the patient to re-absorb, from the cells of her or his tissues, the mass of liquids subtracted from the plasmatic part of the blood; in a further aspect according to any one of the preceding aspects, the parameter of the individual comprises an index which is a function of the quantity of liquid that displaces from the interstitial space of the patient's body to the intravascular space thereof.

In a 7th aspect according to any one of the preceding aspects, the parameter of the individual (IR) comprises a refilling index, alternatively from:

$$IR = \frac{\Delta BV\%}{\Delta WL\%}$$

or from:

$$IR = \frac{\Delta WL\%}{\Delta BV\%}.$$

where ΔBV % is the relative variation of blood volume, i.e. the variation in blood volume as a ratio of the total blood volume, and ΔWL % is the variation in weight loss, i.e. the weight loss as a ratio of the total weight of the individual or the weight of the individual's body water.

In an 8th aspect according to any one of the preceding aspects, the control process (or the control unit) receives in input a minimum threshold value and/or a maximum threshold value of acceptability for the desired value of the individual's parameter.

In a 9th aspect according to the preceding aspect, the minimum threshold value is comprised between 0.9 and 1.1.

In a 10th aspect according to the preceding aspect 8, or aspect 9, the maximum threshold value is comprised between 1.1 and 1.3.

In an 11th aspect according to any one of the preceding aspects, the verification comprises verifying whether:

$$\frac{\Delta BV\%(t)}{WL(t)} = \frac{RI(t)}{TW}$$

where ΔBV % (t) is the relative variation of blood volume at time t, WL(t) is the weight loss at time t, RI (t) is the desired refilling index at time t, TW is a weight value of the individual.

In a 12th aspect according to any one of the preceding aspects from 4 to 11, the weight value of the individual (TW) comprises a value selected from the total body weight of the individual before or after the treatment, the individual's body water weight before or after the treatment, the total body weight or the individual's body water weight at a predetermined moment during the extracorporeal blood treatment.

In a 13th aspect according to any one of the preceding aspects, the desired value is constant during the treatment or follows a predetermined profile according to the treatment time.

In a 14th aspect according to any one of the preceding aspects, the weight loss system comprises an ultrafiltration device (13) for ultrafiltering liquid from the blood chamber to the fluid chamber through the semipermeable membrane (5), and wherein the control unit (20) is configured such as to control the ultrafiltration device on the basis of the verification.

In a 15th aspect according to any one of the preceding aspects, the weight loss system comprises an infusion device (18, 19) for infusing liquid into the extracorporeal circuit, and the control unit (20) is configured such as to control the infusion device on the basis of the verification.

In a 16th aspect according to any one of the preceding aspects, a supply system (16, 17) is comprised for supplying a treatment fluid at a predetermined composition to the fluid chamber (4), the control unit (20) being configured such as to control the supply system on the basis of the verification.

A 17th independent aspect relates to an extracorporeal blood treatment apparatus, comprising: a blood treatment device (2) having a blood chamber (3) and a fluid chamber (4) separated from one another by a semipermeable membrane (5); an extracorporeal blood circuit (6) connected to the blood chamber such as to transport blood from an individual (7) to the blood chamber (3) and to return the blood from the blood chamber to the individual; means for determining an indicative value of a variation in blood, volume (ΔBV) of the individual (7) subjected to the extracorporeal blood treatment; a sensor (14) configured such as to emit at least a signal indicating the weight loss of the individual (7) subjected to the extracorporeal blood treatment; a weight loss system for actuating the weight loss of the individual during the extracorporeal blood treatment; a control unit (20) configured for performing following operations: receiving the signal destined for calculating the weight loss of the individual (7); receiving the value indicating the variation in blood volume ($\Delta BV$) of the individual (7); acquiring a desired value ($IR_{des}$;$K_{des}$), of an individual's parameter (IR;K), the individual's parameter (IR;K) being a function of an index dependent on the ability of the patient to absorb from the cells of the same individual's tissues the mass of liquid subtracted from the plasmatic part of the blood; determining a calculated value (IR;K) of the parameter of the individual as a function of the blood volume variation ($\Delta BV$) and a weight loss variation ($\Delta WL$) of the individual; controlling the weight loss system on a basis of the desired value ($IR_{des}$; $K_{des}$) of the parameter of the individual and the calculated value (IR;K) of the parameter of the individual.

An 18th independent aspect comprises an extracorporeal blood treatment apparatus, comprising: a blood treatment device (2) having a blood chamber (3) and a fluid chamber (4) separated from one another by a semipermeable membrane (5); an extracorporeal blood circuit (6) connected to the blood chamber such as to transport blood from an individual (7) to the blood chamber (3) and to return the blood from the blood chamber to the individual; means for determining an indicative value of a variation in blood volume ($\Delta BV$) of the individual (7) subjected to the extracorporeal blood treatment; a sensor (14) configured such as to emit at least a signal indicating the weight loss of the individual (7) subjected to the extracorporeal blood treatment; a weight loss system for actuating the weight loss of the individual during the extracorporeal blood treatment; a supply system (16, 17) for supplying a treatment fluid at a predetermined composition to the fluid chamber (4); a control unit (20) configured to perform following operations: receiving the signal destined to the calculation of the weight loss of the individual (7), receiving the indicative value of the variation of blood volume ($\Delta BV$) of the individual (7); acquiring a desired value ($IR_{des}$; $K_{des}$) of a parameter of the individual (IR; K), the parameter of the individual (IR, K) being a function of an index depending on the ability of the patient to absorb from the cells of his or her own tissues the mass of liquids subtracted from the plasmatic part of the blood; determining a calculated value (IR; K) of the parameter of the individual as a function of the variation in blood volume ($\Delta BV$) and a variation in weight loss ($\Delta WL$) of the individual; controlling the supply system on the basis of the desired value ($IR_{des}$) of the parameter of the individual and the calculated value (IR) of the parameter of the individual.

In a 19th aspect according to the preceding aspect, the control unit (20) is configured to be able to vary the composition, in particular the conductivity of the composition or the concentration of at least a substance, for example sodium, of the composition, on the basis of the desired value ($IR_{des}$) of the parameter of the individual and the calculated value (IR) of the parameter of the individual.

In a 20th aspect according to any one of the preceding aspects from 17 to 19, the means for determining an indicative value of a blood volume variation ($\Delta BV$) of the individual (7) comprise a transducer provided in the extracorporeal blood circuit (6) for emitting at least a signal destined for calculation of an indicative value of the blood volume variation ($\Delta BV$) of the individual (7) subjected to extracorporeal blood treatment.

In a 21st aspect according to the preceding aspect, the means for determining an indicative value of a blood volume variation ($\Delta BV$) of the individual (7) comprise a calculating unit receiving in input the signals destined for calculation of an indicative value of the blood volume variation ($\Delta BV$) coming from the transducer and configured to calculate an indicative value of the blood volume variation ($\Delta BV$) of the individual (7) undergoing the extracorporeal blood treatment.

In a 22nd aspect according to any one of preceding aspects from 17 to 21, the means for determining an indicative value of a blood volume variation ($\Delta BV$) of the individual (7) comprise a sensor (10) predisposed in the extracorporeal blood-circuit (6) to emit at least an indicative signal of the blood volume variation ($\Delta BV$) of the individual (7) undergoing the extracorporeal blood treatment.

In a 23rd aspect according to the preceding aspect, the sensor (10) comprises a transducer predisposed in the extracorporeal blood circuit (6) for emitting at least a signal destined for calculating an indicative value of the variation of the blood volume ($\Delta BV$) of the individual (7) undergoing the extracorporeal blood treatment.

In a 24th aspect according to the preceding aspect, the sensor (10) comprises a calculating unit receiving in input the signals destined for calculating the indicative value of the blood volume variation ($\Delta BV$) coming from the transducer and configured to calculate an indicative value of the blood volume variation ($\Delta BV$) of the individual (7) undergoing the extracorporeal blood treatment.

In a 25th aspect according to any one of preceding aspects from 17 to 24, the control unit (20) is configured so as to verify whether a relative blood volume variation ($\Delta BV/BV$) and the relative weight loss variation ($\Delta WL/WL$) of the individual is in a predetermined relation with the desired value (IRdes) of the parameter of the individual and to control the system of weight loss on the basis of the verification, the relative blood volume variation ($\Delta BV/BV$) being given by the ratio between the blood volume variation ($\Delta BV$) and the total blood volume (BV), the relative variation in weight loss ($\Delta WL/TW$; $\Delta WL/BWW$) being given by the ratio between the weight loss variation ($\Delta WL$) and the total weight of the individual (TW) or the weight of the body water (BWW) of the individual.

In a 26th aspect according to any one of the preceding aspects from 17 to 25, the control unit (20) the control unit (20) is configured to verify whether a ratio between the percentage relative variation of blood volume ($\Delta BV/BV$ %) and the percentage relative variation of weight loss ($\Delta WL/TW$ %; $\Delta WL/BWW$ %) of the individual is in a predetermined relation with a desired value (IRdes) and to control the weight loss system on the basis of the verification, the percentage relative variation of brood volume ($\Delta BV$ %) being given by the ratio between blood volume variation ($\Delta BV$) and the total blood volume (BV) multiplied by a factor 100, the percentage relative variation of weight loss ($\Delta WL/TW$ %; $\Delta WL/BWW$ %) being given by the ratio between the variation in weight loss ($\Delta WL$) and the total weight of the individual (TW) or the weight of blood water (BWW) of the individual multiplied by a factor 100.

In a 27th aspect according to any one of the preceding aspects from 17 to 26, the control unit (20) is configured to carry out the operations of determining the calculated value (IR) and the control of the weight loss system, in an iterative way during the treatment for a predetermined number of times.

In a 28th aspect according to any one of the preceding aspects from 17 to 27, the control unit (20) is configured to acquire the desired value (IRdes) of a parameter of the individual by receiving a weight value of the individual and determining the desired value (IRdes) as a function of the weight value.

In a 29th aspect according to any one of the preceding aspects from 17 to 28, the control unit (20) is configured to receive an optimal value of the individual (RI) or a plurality of optimal values of the parameter of the individual (RI) or an optimal profile of the parameter of the individual (RI).

In a 30th aspect according to any one of the preceding aspects from 17 to 29, the parameter of the individual (IR) comprises a refilling index defined by a function of the ratio between the variation of the blood volume ($\Delta BV$), and the weight loss variation ($\Delta WL$), i.e:

$$IR = f\left(\frac{\Delta BV}{\Delta WL}\right).$$

In a 31st aspect according to any of the preceding aspects from 17 to 30, the parameter of the individual (IR) comprises a refilling index defined by a function of the ratio between the relative variation of blood volume ($\Delta BV/BV$), and the relative weight loss variation ($\Delta WL/TW$; $\Delta WL/BwW$), i.e:

$$IR = f\left(\frac{\frac{\Delta BV}{BV}}{\frac{\Delta WL}{TW}}\right) \text{ or } IR = f\left(\frac{\frac{\Delta BV}{BV}}{\frac{\Delta WL}{BWW}}\right)$$

In a 32nd aspect according to any one the preceding aspect from 17 to 31, the parameter of the individual (IR) comprises a refilling index defined alternatively by:

$$IR = \left(\frac{\frac{\Delta BV}{BV}\%}{\frac{\Delta WL}{TW}\%}\right) \text{ or } IR = \left(\frac{\frac{\Delta BV}{BV}\%}{\frac{\Delta WL}{BWW}\%}\right)$$

or by:

$$IR = \left(\frac{\frac{\Delta WL}{TW}\%}{\frac{\Delta BV}{BV}\%}\right) \text{ or } IR = \left(\frac{\frac{\Delta WL}{BWW}\%}{\frac{\Delta BV}{BV}\%}\right)$$

where $\Delta BV/BV$ % is the percentage relative blood volume variation, i.e. the ratio between the variation of hematic volume ($\Delta BV$) and the total blood volume (BV) multiplied by a value 100, $\Delta WL/TW$ % is the percentage relative blood loss variation, i.e. the ratio between the weight loss variation ($\Delta WL$) and the total weight (TW) of the individual multiplied by a value 100, and $\Delta WL/BWW$ % is the percentage relative weight loss variation, i.e. the ratio between the weight loss variation ($\Delta WL$) and the weight of the body water of the individual multiplied by a value 100.

In a 33rd aspect according to aspect 29, the control unit (20) is configured to receive a minimum threshold value and/or a maximum threshold level of acceptability for the optimal value.

In a 34th aspect according to the preceding aspect, the minimum threshold value is comprised between 0.9 and 1.1.

In a 35th aspect according to the preceding aspect or aspect 33, the maximum threshold value is comprised between 1.1 and 1.3.

In a 36th aspect according to aspects 25 or 26, or according to any one of the preceding aspects from 27 to 35, when depending on aspect 25 or aspect 26, the verification comprises verifying whether:

$$\frac{\frac{\Delta BV}{BV}(t)}{WL(t)} = \frac{IR(t)}{TW} \text{ or whether } \frac{\frac{\Delta BV}{BV}(t)}{WL(t)} = \frac{IR(t)}{BWW}$$

where ($\Delta BV/BV$)(t) is the relative variation of blood volume at time t, WL(t) is the weight loss at time t, IR(t) is the desired refilling index at time t, TW is a weight value of the individual, BWW is the weight of the body water of the individual.

In a 37th aspect according to aspects 25 or 26, or according to any one of preceding aspects from 27 to 36, when depending on aspect 25 or 26, the weight value of the individual (TW) comprises a value selected from the total body weight of the individual (TW) before or after the treatment, the individual's body water weight (BWW) before or after the treatment, the total body weight or the individual's body water weight at a predetermined moment during the extracorporeal blood treatment.

In a 38th aspect according to any one of preceding aspects from 17 to 37, the desired value ($IR_{des}$) is constant during the treatment or follows a predetermined profile according to the treatment time.

In a 39th aspect according to any one of preceding aspects from 17 to 38, the weight loss system comprises an ultrafiltration device (13) for ultrafiltering liquid from the blood chamber to the fluid chamber through the semipermeable membrane (5), and wherein the control unit (20) is configured to control the ultrafiltration device on the basis of the desired value (IRdes) of the parameter of the individual and the calculated value (IR) of the parameter of the individual.

In a 40th aspect according to any one of preceding aspects from 17 to 39, the weight loss system comprises an infusion device (18, 19) for infusing liquid into the extracorporeal circuit, and wherein the control unit (20) is configured such as to control the infusion device on the basis of the desired value ($IR_{des}$) of the parameter of the individual and the calculated value (IR) of the parameter of the individual.

In a 41st aspect according any one of preceding aspects from 17 to 40, the apparatus comprises a supply system (16, 17) for supplying a treatment fluid at a predetermined composition to the fluid chamber (4), the control unit (20) being configured to control the supply system on the basis of the desired value ($IR_{des}$) of the parameter of the individual and the calculated value (IR) of the parameter of the individual.

In a 42nd aspect according to any one of preceding aspects from 17 to 41, the apparatus comprises a supply system (16, 17) for supplying a treatment fluid at a predetermined composition to the fluid chamber (4), the control unit (20) being configured to be able to vary the composition, in particular the conductivity of the composition or the concentration of at least a substance, for example sodium, of the composition, on the basis of the desired value (IRdes) of the parameter of the individual and the calculated value (IR) of the parameter of the individual.

In a 43rd aspect according to any one of preceding aspects from 17 to 42, the desired value (IRdes) of the parameter of the individual (IR) is the desired refilling index of the patient.

In a 44th aspect according to any one of preceding aspects from 17 to 43, the desired value ($K_{des}$) of the parameter of the individual (IR;K) is a function of the desired refilling index ($IR_{des}$) of the patient.

In a 45th aspect according to any one of preceding aspects from 17 to 44, desired value ($K_{des}$) of the parameter of the individual (IR;K) is an inversely proportional function of the desired refilling index ($IR_{des}$) of the patient.

In a 46th aspect according to any one of preceding aspects from 17 to 45, the desired value (Kdes) of the parameter of the individual (IR;K) is defined by the ratio between the rate of weight loss (WLR) and the desired refilling index ($IR_{des}$):

$$K_{des} = \left(\frac{WLR_0}{IR_{des}}\right) = \left(\frac{WL_{tot}}{T_{tot} \cdot IR_{des}}\right)$$

in which $WL_{tot}$ is the total weight loss and $T_{tot}$ is the total treatment time.

Further characteristics and advantages of the present invention will more fully emerge from the detailed description that follows of at least an embodiment of the invention, illustrated by way of non-limiting example in the accompanying figures of the drawings.

DESCRIPTION OF THE DRAWINGS

The description will be carried out in the following with reference to the accompanying figures of the drawings, provided by way of non-limiting example, in which.

DETAILED DESCRIPTION

Figure 1:
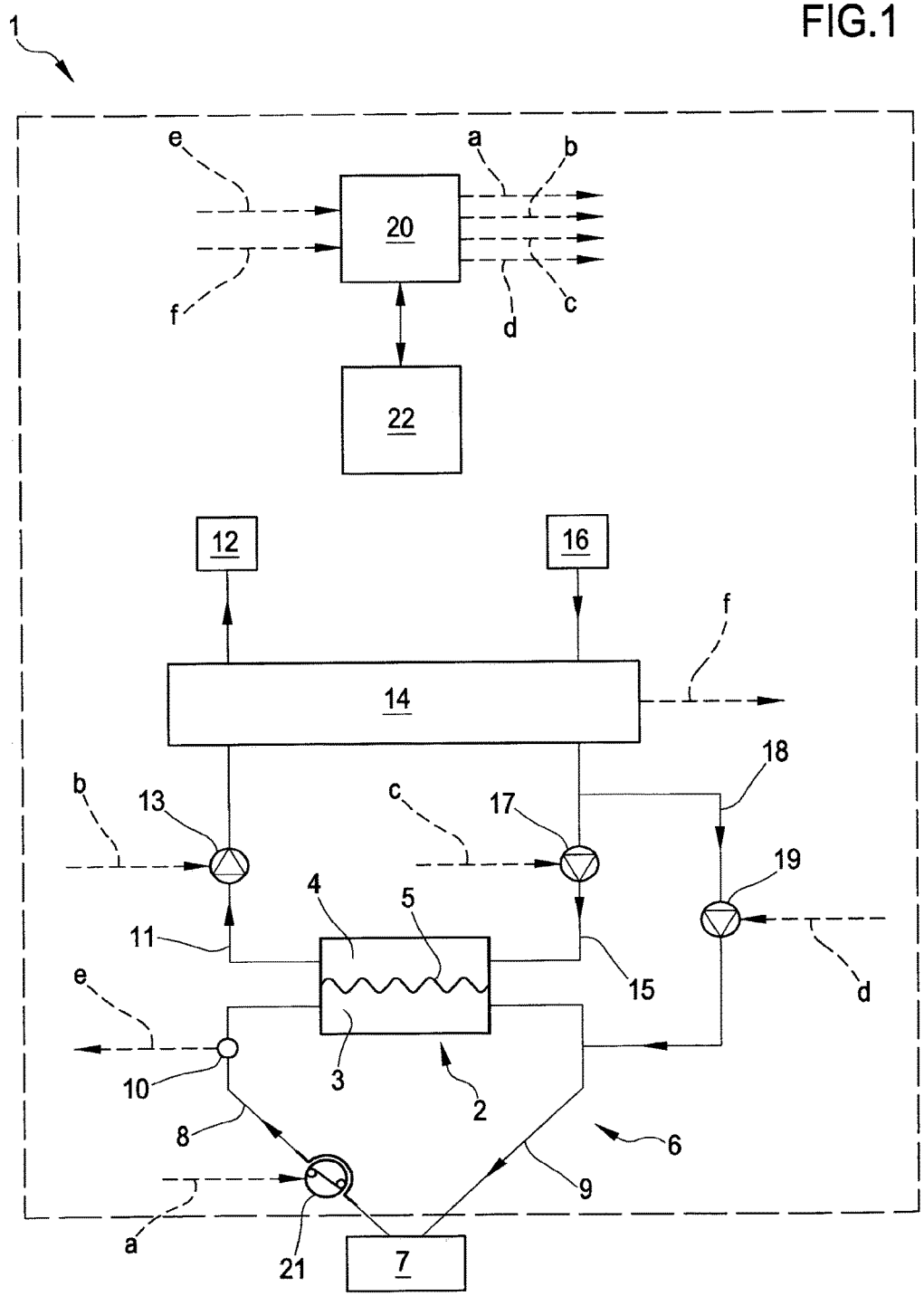
FIG. 1 is a diagram of an extracorporeal blood apparatus according to an embodiment of the present invention.

Referring to the accompanying figures, 1 denotes an apparatus for extracorporeal blood treatment, which, in the present embodiment, includes an apparatus for hemodiafiltration. The extracorporeal blood treatment apparatus can include any one of the hemodialysis or blood (dia)filtration apparatus of the prior art. Reference numeral 2 denotes a blood treatment device, for example a hemofilter, a hemodiafilter, a plasma filter, a dialysis filter, a membrane oxygenator or a further unit also destined to process the blood removed from the patient, having a blood chamber 3 and a fluid chamber 4 separated by a semipermeable membrane 5.

Reference numeral 6 denotes an extracorporeal blood circuit connected to the blood chamber 3 for transporting blood from an individual 7 to the blood chamber 3 and for returning the blood from the blood chamber 3 to the individual 7. The blood circuit 6 comprises a removal line 8 (arterial line) and a return line 9 (venous line). The removal line 8 and return line 9 can include any one of the arterial and venous lines of known type used in an apparatus for hemodialysis or hemo(dia)filtration. In particular, the removal line 8 and return line 9 can be equipped with and/or connected to various sensors and actuators of known type (for example, pressure sensors, blood presence sensors or patient presence sensors, liquid level sensors, air presence sensors, blood transport pumps, infusion liquid transport pumps, automatic block valves, liquid level regulation devices, etc.) for the control and monitoring of the circuit itself, and to various devices of known type (gas-liquid separation devices, removal-injection access sites, manual clamps, service lines, etc.) for performing various operations on the circuit.

The apparatus further comprises means for determining an indicative value of a variation in blood volume (ΔBV) of the individual (7) subjected to the extracorporeal blood treatment. The means comprise a transducer predisposed in the extracorporeal blood circuit (6) for emitting at least a signal destined for calculation of an indicative value of the blood volume variation (ΔBV) of the individual (7) subjected to extracorporeal blood treatment. As also clarified in the following, the transducer will read a property of the blood (for example an optical reading) and generates in output a signal (for example in tension) proportional to the property.

The transducer might emit a signal that is inversely proportional to the concentration of haemoglobin in the blood in various successive temporal instants. The means for determining the indicative value of the variation in blood volume ΔBV further comprise a calculating unit (which might be integrated directly in the transducer or, more commonly, be the control unit 20 of the apparatus) receiving in input the signals of the transducer relative to the concentration of hemoglobin and useful for the calculation of the indicative value of the variation in blood volume ΔBV. The calculating unit, with appropriate known algorithms, is configured so as to calculate the indicative value of the variation in blood volume ΔBV of the individual 7 subjected to the extracorporeal blood treatment, the variation read between two successive readings of the transducer. In general the calculating unit, i.e. the control unit 20, will determine a relative variation in blood volume ΔBV/BV, i.e. the variation in blood volume ΔBV divided by the total blood volume BV (the value thus-obtained is therefore a dimensionless value.

For simplicity of reading in general, the calculating unit, i.e. the control unit 20, will determine a relative percentage variation of blood volume ΔBV/BV %, i.e. the variation in blood volume ΔBV divided by the total blood volume BV multiplied by a factor 100.

In fact the means for determining the indicative value of a variation in blood volume ΔBV of the individual 7 comprise a sensor 10 predisposed in the extracorporeal blood circuit 6 for emitting at least a signal indicating the variation in blood volume ΔBV of the individual 7 subjected to the extracorporeal blood treatment and in turn the sensor 10 comprises the transducer and the calculating unit receiving in input the signals destined for calculating the value indicating the variation in blood volume ΔBV coming from the transducer.

Reference numeral 10 therefore (by way of example) denotes a sensor predisposed in the extracorporeal blood circuit (in the non-limiting example located on the removal line 8) for emitting at least the signal indicative of the variation of blood volume of the individual subjected to extracorporeal blood treatment. This sensor 10, of known type, may include for example an optical or acoustic sensor. In the illustrated embodiment the blood volume variation sensor 10 comprises a sensor for estimating the hemoglobin useful in calculating the relative variation in blood volume.

The signals emitted by the hemoglobin-estimating sensor during treatment are used, in a known way, in determining the blood volume variation in the individual 7.

The sensor 10 installed on-board the machine enables, for example, detecting: at regular intervals of time, the concentration of blood haemoglobin in the arterial line (or alternatively in the venous line). From these measurements of concentration it is possible to arrive (directly by mean of the intelligence possibly present in the sensor, or preferably via the control unit present on-board the machine, to the variation in blood volume in a general instant, exploiting the fact that the protein (haemoglobin) is not removed from the filter and therefore its quantity remains constant over time. Therefore a variation in concentration of the haemoglobin is only due to the variation of the volume in which it is distributed. Examples of blood volume variation are described in document WO2011/138650 A2.

The apparatus 1 comprises a weight loss system to actuate the weight loss of the individual during the extracorporeal blood treatment. In the illustrated example the weight loss system includes a drain line 11 connected to a fluid chamber outlet 4 for removing a discharge liquid from the chamber and sending it to a drainage 12 (bag or discharge). Reference number 13 denotes a discharge pump for moving the discharge liquid. Reference numeral 14 denotes a sensor configured such as to emit at least a signal indicating the weight loss of the individual subjected to extracorporeal blood treatment. In the illustrated example, the sensor 14 comprises any one of the sensor means of known type used for detecting the patient weight loss in an ultrafiltration, hemodialysis or blood(dia)filtration apparatus. In the illustrated example, in which the apparatus 1 is a hemodiafiltration apparatus, the sensor 14 can comprise, for example, the following systems of known type: a two-flowmeter system of (one upstream and one downstream of the filtering unit 2), or a differential flow meter, or a system of scales, or a control system of the filling of predetermined volumes, or an ultrafiltration flow sensor in a fluid-balancing system with variable volume chambers, or still other systems of known type.

The extracorporeal treatment apparatus can further comprise a system for supplying a fresh treatment fluid in a predetermined composition to the fluid chamber 4. The supply system can comprise any one of the supply systems of known type used to supply a dialysis and/or replacement fluid in a hemodialysis or hemo(dia)filtration apparatus (for example of the type with in-line preparation of the treatment fluid from water and concentrates of the type sourcing from a batch-type source such as one, or more bags of fluid). In the illustrated example the supply system comprises a supply line 15 connected to an inlet of the fluid chamber 4, a source 16 of the treatment fluid (batch-type or in-line preparation type) and a supply pump 17. The sensor 14 in this case will be connected to the supply line 15 such as also to take into account, when determining the individual's weight loss, the flow of the treatment fluid, in particular dialysis fluid entering the fluid chamber 4 and/or possibly replacement fluid infused into the extracorporeal circuit 6. In the illustrated example, the source 16 comprises a device for the in-line preparation of a treatment fluid having a predetermined concentration. The preparation device can comprise any of the devices of known type used in a hemodialysis or hemo(dia)filtration machine. In particular the preparation device can prepare the treatment fluid starting from water and concentrates by using of one or more sensors, for example, an electrical conductivity sensor (or another type of sensor for determining the composition of the dialysis solution) in order to determine, in a known way, the composition of the prepared fluid. The structure and functioning of the preparation device is known and therefore will not be further detailed. In use, the hemodiafiltration apparatus operates in a known way to effect a predetermined weight loss in the individual, giving rise to an ultrafiltration device for ultrafiltering liquid from the blood chamber 3 to the fluid chamber 4 through the semipermeable membrane 5. In particular, the ultrafiltration is carried out by exploiting the pressure difference at the two sides of the membrane 5 (transmembrane pressure, or TMP) and the resulting convective transport of liquid generated by the discharge pump 13 which enables having a pressure in the chamber fluid 4 that is lower than the pressure in the blood chamber 3. The ultrafiltration means are substantially of known type and therefore do not require further explanation. Any other ultrafiltration means of known type can be used.

The apparatus can also include an infusion device for infusing liquid into the extracorporeal circuit. In the illustrated example the infusion device includes an infusion line 18 and an infusion pump 19 for movement of the infusion fluid. In the illustrated example the infusion line 18 is connected in a branched relationship with the supply line 15, from a branch point positioned downstream of the sensor 14. The infusion line can be connected to a batch source of infusion fluid. In the illustrated example the infusion line 18 is connected to the return line 9 (post-dilution), although in addition to or as an alternative to the line 18 an infusion line can be provided, not shown, connected to the removal line 8 (pre-dilution).

The extracorporeal blood treatment apparatus is also provided with at least a control unit 20. The control unit 20 can comprise one or more digital modules, for example of the microprocessor type, or one or more analog modules, or a suitable combination of digital and analog. As illustrated in the example of FIG. 1, the control unit 20 is connected to the blood pump 21 (arrow a) and/or with the dialysate pump 13 (arrow b) and/or with the dialysis pump 17 (arrow c) and/or with the infusion pump 19 (arrow d), as well as with the sensor 10 (arrow e) configured to emit a signal indicating of the variation in blood volume of the individual subjected to extracorporeal blood treatment and with the sensor 14 (arrow f) configured such as to emit at least a signal indicating of the weight loss of the individual subjected to extracorporeal blood treatment.

Obviously, the connections a, b, c, d, e and f can be mono- and bi-directional connections according to the needs of the apparatus (the direction of the arrow in the figure has been inserted non-limitingly).

The control unit 20 will be connected in a known manner to all sensors and/or actuators present on the apparatus such as (by way of example) pressure sensors of the arterial and venous expansion chambers and optionally, if present, with auxiliary pressure sensors. Further, the control unit can be connected to the fluid intercept bodies of the extracorporeal circuit. The control unit 21 is also in communication with the bubble detecting device, if present (not shown), with the module 16 (if for in-line preparation) and possibly with the actuators on the blood and/or dialysis lines.

Also present is a user interface 22 which enables entering data, such as information on the patient, relating to desired weight loss, treatment time, significant parameters of the treatment and/or the individual etc; the user interface also shows and/or displays data in output, such as information on the patient, information on the treatment and/or significant parameters of the treatment and/or of the individual, sound and/or visual alarms etc.

The user interface 22 can be a graphic user interface, such as a touch screen.

Naturally the user interface 22 is connected to the control unit 21 bidirectionally, for data exchange. The control unit 21 is configured or programmed to perform the procedures described below. In a case in which the control unit is of the programmable type, this unit is connected with a data carrier, for storing instructions, that when run by the control unit determines the carrying-out of the procedures that will be described below. The data carrier may comprise a mass storage, for example, optical or magnetic, a re-programmable memory (EPROM, FLASH) or a memory of another sort.

In particular, the control unit 20 is configured to receive signals indicating variation of blood volume and signals indicating weight loss during extracorporeal blood treatment, in order to verify whether the relationship between the relative variation of blood volume $\Delta BV/BV$ and the relative variation in the weight loss $\Delta WL/TW$ of the individual is in a predetermined relationship with a desired value $IR_{des}$, and to control the weight loss system on the basis of the above verification.

The control unit 20 is configured to carry out the above receiving operations of verification and control signals iteratively during treatment.

The control unit 20 can optionally be configured to receive a weight value of the individual and to determine the abovementioned desired value on the basis of this weight value. For example, the operator can enter the weight value of the individual and the control unit stored in a pre-memorised table to acquire a corresponding desired value of the individual's parameter. The patient's weight can be the only discriminating parameter for retrieving the desired value of the individual's parameter, or the operator can supply (or the apparatus can request) further data such as the sex of the patient and/or the age and/or ethnic origin, and so on.

Naturally the control unit can directly receive the desired value as an input by the operator.

The desired value can be a fixed value or a profile of desired values (discrete or continuous) that is variable over time.

The control unit 20 can optionally be configured to receive at least an optimal value of a parameter of the individual and to determine the abovementioned desired value according to a weight value and the mentioned optimum value. The above parameter of the individual provides useful information for understanding the response of a patient undergoing dialysis, in particular of his or her behaviour relating to what is known as vascular "refilling", i.e. the amount of fluid that moves from the interstitial space of the patient's body to the intravascular space. During treatment the mass of accumulated liquids is subtracted from the blood plasma, which then has the task of reabsorbing from the cells of the tissues. Physiologically, this reconstitution (refilling) occurs quite slowly because it in turn depends on the permeability of the cell membrane and the extra-intracellular gradient, so that violent removal can cause significant side effects such as collapse and cramps. The control system of the apparatus is able to ensure optimal accuracy of extractions and treatment comfort by following this parameter and the desired value (or performance) thereof during treatment.

The above parameter of the individual optionally comprises a refilling index IR that can be defined by a function of the ratio between the variation in blood volume ($\Delta BV$) and the variation in weight loss ($\Delta WL$), i.e:

$$IR = f \frac{\Delta BV}{\Delta WL}$$

The individual's parameter (IR) comprises a refilling index defined by a function of the ratio between the relative variation of blood volume ($\Delta BV/BV$), and the relative variation of weight loss ($\Delta WL/TW$; $\Delta WL/BWW$), i.e.:

$$IR = f\left(\frac{\frac{\Delta BV}{BV}}{\frac{\Delta WL}{TW}}\right) \text{ or } IR = f\left(\frac{\frac{\Delta BV}{BV}}{\frac{\Delta WL}{BWW}}\right)$$

In general the individual's parameter (IR) comprises a refilling index defined, alternatively, by:

$$IR = \left(\frac{\frac{\Delta BV}{BV}\%}{\frac{\Delta WL}{TW}\%}\right) \text{ or } IR = \left(\frac{\frac{\Delta BV}{BV}\%}{\frac{\Delta WL}{BWW}\%}\right)$$

or by $$IR = \left(\frac{\frac{\Delta WL}{TW}\%}{\frac{\Delta BV}{BV}\%}\right) \text{ or } IR = \left(\frac{\frac{\Delta WL}{BWW}\%}{\frac{\Delta BV}{BV}\%}\right)$$

where $\Delta BV/BV$ % is the relative variation of blood volume ($\Delta BV$), i.e. the variation in blood volume (BV) multiplied by a value 100, $\Delta WL/TW$ % is the relative percentage value of weight loss, i.e. the variation in weight loss ($\Delta WL$) related to the total weight (TW) of the individual multiplied by a value 100, and $\Delta WL/BWW$ % is the relative percentage variation of weight loss, i.e. the ratio between the variation in weight loss ($\Delta WL$) and the weight of the body water of individual multiplied by 100.

Briefly the above-reported equations can also be expressed in the following notation:

$$IR = \frac{\Delta BV\%}{\Delta WL\%} \text{ or by } IR = \frac{\Delta WL\%}{\Delta BV\%}$$

where $\Delta BV$ % is the relative percentage value of blood volume, i.e. the ratio between the variation in blood volume and the total blood Volume, and $\Delta WL$ % is the relative percentage variation in weight loss, i.e. the ratio between the weight loss and the total weight of the individual or the weight of the corporeal water of the individual.

Obviously, the individual's parameter will be proportional to the refilling index IR and in particular can be proportional to the refilling index IR or coinciding with the refilling index.

In the description that follows, we will examine the case relating to the second definition of the above-evidenced index IR $$\left(IR = \frac{\Delta WL\%}{\Delta BV\%}\right),$$

but naturally the same approach can be obtained by exploiting the first definition of the refilling index or, even a factor proportional to one or the other definition of the refilling index or any function thereof and therefore the detailed description below is not intended as a factor that limits the invention.

The control unit 20 may also be configured to receive a minimum threshold value and/or a maximum threshold value of acceptability for the aforementioned desired parameter of the individual. In a case in which the individual parameter is the refilling index, the above-mentioned minimum threshold value can be comprised, for example, between 0.9 and 1.1, while the above-mentioned maximum threshold value can be comprised, for example, between 1.1 and 1.3.

The above-cited verification can comprise verifying if:

$$\frac{\frac{\Delta BV}{BV}(t)}{WL(t)} = \frac{IR(t)}{TW} = \frac{IR_{des}(t)}{TW}$$

where $\Delta BV/BV(t)$ is the relative variation of blood volume at time t, $WL(t)$ is the weight loss at time t, $IR(t)$ is the desired refilling index at time t, TW is a weight value of the individual. Even TW can be a value $TW(t)$ dependent on the treatment time, for example if we consider the value $TW(t)$ of the patient's weight (total weight or weight of body water) at time t, i.e. taking into account the weight loss $WL(t)$ reached precisely at time t. In this case the weight at time t will be $TW(t)=TW_0-WL(t)$, where $TW_0$ is the patient's weight (total weight or weight of body water) at the beginning of treatment.

The above-mentioned weight value of the individual can optionally comprise a value selected from between the total body weight of the individual before or after the treatment, the weight of the body water of the individual before or after the treatment, the total body weight or the weight of the body water of the individual at a Specific time during the extracorporeal treatment of blood.

The desired value $IR_{des}$ can be constant during the treatment, or that it can follow a predetermined profile (e.g. presettable by the operator via the user interface of the treatment apparatus) as a function of the treatment time.

The flow chart of the steps implemented by the method as described above is shown in FIG. 2 and is described in further detail in relation to the first example of the control procedure as set out below.

First Example

Let us suppose that for a certain patient it has been verified that, on the basis of the dialysis treatment to which she or he was previously subjected and the consequent physiological reactions, an optimal value of the refilling index is 1.0 constant for the entire treatment. This value $IR_{DES}=1.0$ is therefore used as the setting value.

$IR_{DES}=1.0$

This value is entered by the operator as a setting value of the treatment using the user interface of the apparatus.

The operator also enters a value of the patient's weight, for example using the user interface of the apparatus. This value may be the weight of the patient TW before treatment (so-called "wet weight"), or the weight of the patient TW after treatment (so-called "dry weight"), or the weight of the body water of the patient BWW (before or after treatment).

The weight of the body water BWW is calculable, as is known, as a function of the total weight of the patient TW, for example by means of a proportionality factor (sometimes called a body water distribution volume) that normally can be considered to be between 50% and 60%, for example 55%. Therefore, assuming for example that the dry weight of the patient TW (end of treatment) is 80 kg, the weight of the body water BWW can be calculated at the end of treatment to be 80*0.55=44 kg BWW=44 Kg Other known ways of determining the weight of the water body can still be used, such as systems that consider various factors such as the patient's age, sex, and so on.

The operator can also enter a value of the initial weight loss $WLR_0$ at time $t=T_0=0$. This initial value can be determined by evaluating one or more from among the following criteria: based on experience, on the patient's behaviour in previous treatments, the current situation of the patient before treatment, a treatment time and a drop in indicative total weight which is to be reached, the type of treatment, etc.

Alternatively, the rate of initial weight loss can also be calculated taking into account two different inputs, i.e. the fall in total weight $WL_{tot}$ and the total treatment time $T_{tot}$.

$WLR_0=WL_{tot}/T_{tot}$.

Figure 2:
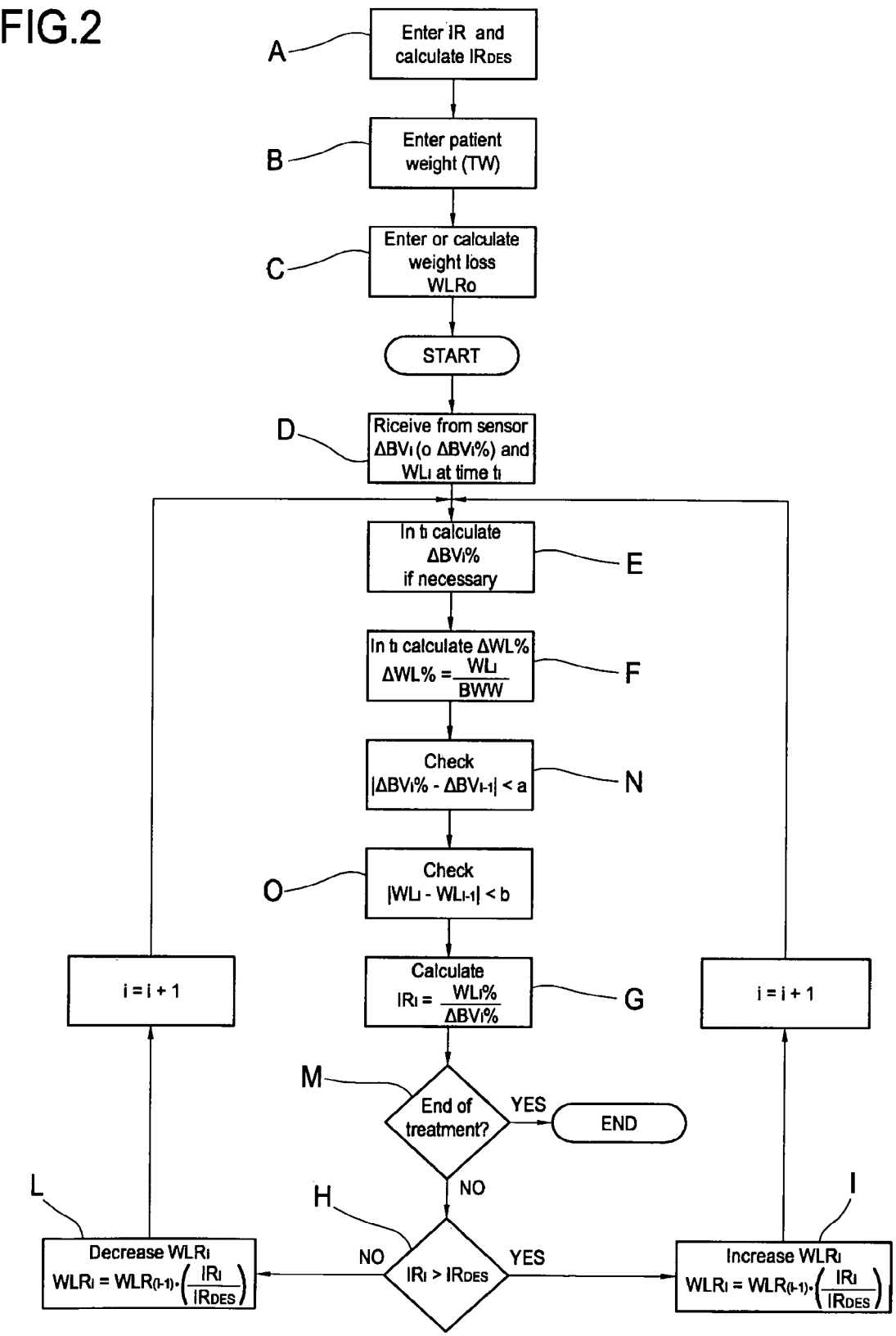
FIG. 2 is a block diagram illustrating the functioning of the invention and the steps of the implemented control method.

The steps of entering the parameters that serve for implementation of the control method are also represented in FIG. 2 in relation to the first three blocks A, B, C upstream of the initial step of treatment (start phase).

At this point the treatment can start. For a certain initial time the control unit controls the weight loss system such as to obtain a rate of weight loss of $WLR_0$. After a certain time $t=T_1$, the control unit 20 receives, from the sensors 10, 14, the corresponding signals (block D) with which the unit itself can determine the relative percentage variation of blood volume $\Delta BV\%_1$ and the weight loss $WL_1$ achieved at time $T_1$ (blocks D and E). The control unit 20 can then calculate (see block F) the relative weight loss $\Delta WL\%_1$ reached at time $T_1$ from $WL_1$ and the total weight BWW:

$\Delta WL\%_1=WL_1/BWW$

The control unit 20 (block G) calculates the ratio:

$IR_1=WL\%_1/\Delta BV\%_1$ and compares (block H) value $IR_1$ thus-calculated with the value of the desired index $IR_{des}$.

Note that with the synthetic indication $\Delta BV\%$ is meant $\Delta BV/BV*100$ and with $\Delta WL\%$ is meant $\Delta WL/TW*100$. If $IR_1$ is equal to $IR_{des}$ then it maintains the same control value as the weight loss rate $WLR_0$, i.e. $WLR_1=WLR_0$.

If, instead, $IR_1>IR_{des}$, this means that the refilling capacity of the patient is relatively good, and the weight loss rate can therefore be increased without affecting the well-being of the patient (block I). The control unit 20 in this case will set a weight loss rate of greater than the current one, using, for example, a criterion of proportionality, for which:

$WLR_1=WLR_0*(IR_1/IR_{des})$

If, instead, $IR_1<IR_{des}$ (block L), this means that the refilling capacity of the patient is relatively poor, for which the weight loss rate will be decreased such as not to affect the well-being of the patient. The control unit 20 in this case will set a weight loss rate of less than the current time, using, for example, the same criterion of proportionality, so that also in this case:

$WLR_1=WLR_0*(IR_1/IR_{des})$

Naturally the control unit 20 can be configured so as to determine the value IR1 and to directly control the weight loss system through, for example, the relation (i.e. without directly comparing $IR_1$ and $IR_{des}$:

$$WLR_1 = WLR_0 * (IR_1/IR_{des})$$

At time $t=T_2$ the control unit receives the signals from the sensors 10 and 14 in order to determine $\Delta BV \%_2$ and $\Delta WL \%_2$, and thus $IR_2 = WL \%_2 / \Delta BV \%_2$, after which it will determine the new value of the weight loss rate according to, for example, the following relation:

$$WLR_2 = WLR_0 * (IR_2/IR_{des})$$

Therefore, in the example described here, the control unit 20 can periodically for a plurality of times during treatment, at a generic instant $t=T_i$, determine the weight loss rate with the generic relation:

$$WLR_i WLR0 = *(IR_i/IR_{des})$$

The treatment can be terminated (block M) when, for example, a certain desired weight loss has been reached, or after a certain desired treatment time, or after a certain desired dialysis dose has been reached, or at the discretion of the physician who can discontinue treatment via the user interface, or according to still other criteria.

It is possible that the initial setting of the treatment might include a desired value of $WLR_0/IR_{des} = K_{des}$, or equivalently $K_{des} = WL_{tot}/(T_{tot}*IR_{des})$ for which the weight loss rate is determined periodically by:

$$WLR_i = K_{des} * IR_i$$

$IR_{des}$ and $K_{des}$, desired values of the individual's parameter, can be both constant or variable over time following a predetermined profile.

Further, at each iteration of the control (for example at the generic time $t=T_i$) there can be an additional safety check (blocks N and O) in which the control unit 20 controls one of the following conditions: a) if, from time $T_{i-1}$ to time $T_i$, the relative percentage blood volume variation has actually been a variation $\Delta BV \% \; i - \Delta BV \%_{i-1}$ which falls within predetermined limits (upper and/or lower), or b) if, from time $T_{i-1}$ to time $T_i$ the actual weight loss value $WL_i - WL_{i-1}$ falls within predetermined limits (upper and/or lower), or c) both of the above conditions a) and b). For example a control can be programmed for if, in a certain period of time (for example $T_i - T_{i-1}$), the blood volume has lowered and/or the weight loss has increased.

Second Example

In a second embodiment $IR_i$ is determined as in the first example and then the error $\varepsilon_i = Ir_i - IR_{des}$ is calculated.

The control unit 20 operates such as to maintain $\varepsilon_i$ at a minimum value during the course of the treatment. Based on the calculation of $\varepsilon_i$ the control unit controls the current value of the weight loss rate $WLR_1$ using a regulator of known type. The control unit, as an alternative or in addition to the action on the weight loss rate, can act on the composition (conductivity) of the treatment fluid (dialysate).

Third Example

The control system operates such that during the treatment at the generic time t the following condition is complied with:

$$RI(t) = \frac{\Delta WL \, \%(t)}{\Delta BV \, \%(t)} = RI_{DES}$$

The control system can define a desired profile of the refilling index $IR_{des}$ as a function of the treatment time. It is also possible to set one or more desired values of the patient weight loss (for example, a final value and/or an intermediate value and/or a series of intermediate values suitable for determining a desired profile over time; it can also set off at least one maximum threshold value and/or a minimum threshold value for the weight loss (for example, a series of threshold values of maximum and/or minimum threshold weight losses can be set, as well as defining one or more bands of safety values for the weight loss as a function of the time, the exceeding of which threshold values or bands of safety values can set off an alarm).

During the course of treatment, at any instant of time $T_1$, $T_2$, $T_3$, ..., $T_i$, ..., the percentage relative variation of partial blood volume $\Delta BV_1\%$, $\Delta BV_2\%$, $\Delta BV_3\%$, ..., $\Delta BV_i\%$, ..., reached at time $T_1$, $T_2$, $T_3$, ..., $T_i$, ..., is desirably proportional to the partial weight loss percentage $\Delta WL_1\%$, $\Delta WL_2\%$, $\Delta WL_3\%$, ..., $\Delta WL_i\%$, ..., reached at the same time $T_1$, $T_2$, $T_3$, ..., $T_i$, ..., with the same proportionality ratio $IR_{des}$, namely:

$$\Delta BV_1 \% = IR_{DES} * \Delta WL_1 \%$$
$$\Delta BV_2 \% = IR_{DES} * \Delta WL_2 \%$$
$$\Delta BV_3 \% = IR_{DES} * \Delta WL_3 \%$$
$$...$$
$$\Delta BV_i \% = IR_{DES} * \Delta WL_i \%$$
$$...$$

where
$$\Delta WL_1 \% = 100 * WL_1 / BWW$$
$$\Delta WL_2 \% = 100 * WL_2 / BWW$$
$$\Delta WL_3 \% = 100 * WL_3 / BWW$$
$$...$$
$$\Delta WL_i \% = 100 * WL_i / BWW$$
$$...$$

for which, in general, the following obtains:

$$\Delta BV_i \% = IR_{des} * 100 * WL_i / BWW$$

If, for example, at time $T_i$ the percentage relative variation of partial blood volume $\Delta BV_i\%$ measured is 3.5%, at the same time Ti the WLi partial weight loss should be:

$$WL_i = BWW * \Delta BV_i \% / IR_{des} * 100$$

In the specific case the following should obtain:

$$WLi = 443.5/1.0 * 100 = 1.54 \, Kg$$

A desired profile of the weight loss can be set (approximate profile, i.e. an approximate profile which it is intended to reach during treatment and which has the function of providing a fault indication if the actual profile obtained based on the actual response of the individual to treatment were to deviate too far from the approximated desired profile) and defined starting from the desired profile (also approximate) of the relative blood volume variation. The approximate desired profile of the variation in blood volume can be defined, for example, by taking account of a desired drop in total weight (approximated) and the patient's weight (dry or wet, the total weight or body water weight).

If the partial refilling index measured during the course of treatment at a certain instant is less than the desired refilling index for that moment, it will be necessary to slow the weight loss rate. If conversely the partial refilling index measured is greater than the desired refilling index, then the weight loss rate can be accelerated. The actual entity of the respective deceleration or acceleration will depend on the type of control system, more or less evolved, which it is intended to adopt.

The invention claimed is:

1. A method of controlling an apparatus for extracorporeal blood treatment, wherein the apparatus comprises a blood treatment device having a blood chamber and a fluid chamber separated from one another by a semipermeable membrane, an extracorporeal blood circuit connected to the blood chamber configured to transport blood from an individual to the blood chamber and to return the blood from the blood chamber to the individual, a blood volume sensor configured to provide a signal corresponding to an indicative value of a blood volume variation of an individual undergoing extracorporeal blood treatment using the apparatus, a sensor configured to emit at least a signal corresponding to a weight loss variation of the individual undergoing the extracorporeal blood treatment; a weight loss system configured for actuating the weight loss of the individual during the extracorporeal blood treatment;

wherein the method comprises:
receiving the signal corresponding to the weight loss variation of the individual;
receiving the indicative value of the blood volume variation of the individual;
acquiring a desired value of a refilling index ($IR_{DES}$), the refilling index being a function of an ability of the individual to absorb a mass of liquid subtracted from the plasmatic part of the blood by the weight loss system from cells of tissues of the individual, wherein the refilling index (IR) is defined by function (I) of a ratio between the blood volume variation ($\Delta BV$) and the weight loss variation ($\Delta WL$):

$$IR = f\left(\frac{\Delta BV}{\Delta WL}\right) \quad (I)$$

determining a calculated value of the refilling index ($IR_{CAL}$) as a function of the blood volume variation and a weight loss variation of the individual; and
controlling the weight loss system on a basis of the desired value of the refilling index ($IR_{DES}$) and the calculated value of the refilling index ($IR_{CAL}$).

2. The method of claim 1, wherein controlling the weight loss system comprises controlling a weight loss rate for the individual ($WLR_i$) as a function (II) of the desired value of the refilling index ($IR_{DES}$) and the calculated value of the refilling index ($IR_{CAL}$):

$$WLR_i = f(IR_{DES}, IR_{CAL}) \quad (II).$$

3. The method of claim 2, wherein controlling the weight loss rate for the individual ($WLR_i$) is a function (III) of an initially set weight loss rate for the individual ($WLR_0$) and the desired value of the refilling index ($IR_{DES}$) and the calculated value of the refilling index ($IR_{CAL}$):

$$WLRi = f\left\{WLB_0, \frac{IR_{CAL}}{IR_{DES}}\right\} \quad (III).$$

4. The method of claim 1, comprising verifying whether a relative blood volume variation and a relative weight loss variation of the individual is in a predetermined relation with the desired value of the refilling index ($IR_{DES}$) and controlling the weight loss system on the basis of the verification, the relative blood volume variation being a ratio between the blood volume variation ($\Delta BV$) and the total blood volume of the individual (BV), the relative weight loss variation being a ratio between the weight loss variation ($\Delta WL$) and the total weight (TW) of the individual or the body water weight (BWW) of the individual.

5. The method of claim 1, comprising verifying whether a ratio between a percentage relative blood volume variation and a percentage relative weight loss variation of the individual is in a predetermined ratio with a desired value and controlling the weight loss system on the basis of the verification, the percentage relative blood volume variation being given by a ratio between blood volume variation ($\Delta BV$) and the total blood volume (BV) multiplied by a factor 100, the percentage relative weight loss variation being given by a ratio between the weight loss variation and the total weight (TW) of the individual or the body water weight (BWW) of the individual multiplied by a factor 100.

6. The method of claim 1, comprising controlling the weight loss system in an iterative way during the treatment for a predetermined number of times.

7. The method of claim 1, comprising acquiring the desired value of the refilling index ($IR_{DES}$) by receiving a weight value of the individual and determining the desired value of the refilling index ($IR_{DES}$) as a function of the weight value of the individual.

8. The method of claim 1, comprising receiving at least one of the following: an optimal value of the refilling index, a plurality of optimal values of the refilling index, an optimal profile over time of the refilling index.

9. The method of claim 4, wherein the refilling index (IR) is a ratio between the relative blood volume variation and the relative weight loss variation according to one of the following:

$$IR = f\left(\frac{\frac{\Delta BV}{BV}}{\frac{\Delta WL}{TW}}\right) \text{ or } IR = f\left(\frac{\frac{\Delta BV}{BV}}{\frac{\Delta WL}{BWW}}\right)$$

where $\Delta BV$ is the blood volume variation, BV is the total blood volume of the individual, $\Delta WL$ is the weight loss variation of the individual, TW is the total weight of the individual, and BWW is body water weight of the individual.

10. The method of claim 5, wherein the refilling index (IR) is defined by:

$$IR = \left(\frac{\frac{\Delta BV}{BV}\%}{\frac{\Delta WL}{TW}\%}\right) \text{ or } IR = \left(\frac{\frac{\Delta BV}{BV}\%}{\frac{\Delta WL}{BWW}\%}\right)$$

or by:

$$IR = \left(\frac{\frac{\Delta WL}{TW}\%}{\frac{\Delta BV}{BV}\%}\right) \text{ or } IR = \left(\frac{\frac{\Delta WL}{BWW}\%}{\frac{\Delta BV}{BV}\%}\right)$$

where ΔBV/BV % is the percentage relative blood volume variation which is a ratio between the blood volume variation and the total blood volume multiplied by a value 100, ΔWL/TW % is the percentage relative blood loss variation which is a ratio between the weight loss variation and the total weight of the individual multiplied by a value 100, and ΔWL/BWW % is the percentage relative weight loss variation which is a ratio between the weight loss variation and the body water weight of the individual multiplied by a value 100.

11. The method of claim 8, comprising receiving either a minimum threshold value of the optimal value of the refilling index or a maximum threshold level of the optimal value of the refilling index, or both a minimum threshold value and a maximum threshold level of the optimal value of the refilling index.

12. The method of claim 11, wherein the minimum threshold value is comprised between 0.9 and 1.1 and wherein the maximum threshold value is comprised between 1.1 and 1.3.

13. The method of claim 1, comprising verifying whether:

$$\frac{\frac{\Delta BV}{BV}(t)}{WL(t)} = \frac{IR(t)}{TW} \text{ or whether } \frac{\frac{\Delta BV}{BV}(t)}{WL(t)} = \frac{IR(t)}{BWW}$$

where ΔBV/BV(t) is the relative blood volume variation at time t, WL(t) is the weight loss at time t, IR(t) is the desired refilling index at time t, TW is a weight value of the individual, BWW is the body water weight of the individual.

14. The method of claim 13, wherein the weight value of the individual comprises a value selected from the following: the total weight of the individual before or after the treatment, the body water weight of the individual before or after the treatment, the total weight of the individual at a predetermined time during the extracorporeal blood treatment, the body water weight of the individual at a predetermined time during the extracorporeal blood treatment.

15. The method of claim 1, wherein the desired value of the refilling index ($IR_{DES}$) is constant during the treatment or follows a predetermined profile according to the treatment time.

16. The method of claim 1, wherein the weight loss system comprises an ultrafiltration device for ultrafiltering liquid from the blood chamber to the fluid chamber through the semipermeable membrane, and wherein the method comprises controlling the ultrafiltration device on the basis of the desired value of the refilling index ($IR_{DES}$) and the calculated value of the refilling index ($IR_{CAL}$).

17. The method of claim 1, wherein the weight loss system comprises an infusion device for infusing liquid into the extracorporeal circuit, and wherein the method comprises controlling the infusion device on the basis of the desired value of the refilling index ($IR_{DES}$) and the calculated value of the refilling index ($IR_{CAL}$).

18. The method of claim 1, wherein the apparatus comprises a supply system for supplying a treatment fluid at a predetermined composition to the fluid chamber, and wherein the method comprises controlling the supply system on the basis of the desired value of the refilling index ($IR_{DES}$) and the calculated value of the refilling index ($IR_{CAL}$).

19. The method of claim 1, wherein the apparatus comprises a supply system for supplying a treatment fluid at a predetermined composition to the fluid chamber, and wherein the method comprises changing the conductivity of the composition or the concentration of at least a substance of the composition on the basis of the desired value of the refilling index ($IR_{DES}$) and the calculated value of refilling index ($IR_{CAL}$).

20. The method of claim 1, comprising verifying whether:

$$(IR_{CAL} = IR_{DES})$$

and, when ($IR_{CAL}$) is equal to $IR_{DES}$, maintaining the weight loss rate;
when ($IR_{CAL}$) is higher than $IR_{DES}$, increasing the weight loss rate; and
when ($IR_{CAL}$) is lower than $IR_{DES}$, decreasing the weight loss rate.

21. The method of claim 1, comprising calculating an error $\varepsilon_i$ as follows:

$$\varepsilon_i = IR_{CAL} - IR_{DES}$$

and minimizing the error during treatment of the individual.

22. A method of controlling an apparatus for extracorporeal blood treatment, wherein the apparatus comprises a blood treatment device having a blood chamber and a fluid chamber separated from one another by a semipermeable membrane, an extracorporeal blood circuit connected to the blood chamber configured to transport blood from an individual to the blood chamber and to return the blood from the blood chamber to the individual, a blood volume sensor configured to provide a signal corresponding to an indicative value of a blood volume variation of an individual undergoing extracorporeal blood treatment using the apparatus,
a sensor configured to emit at least a signal corresponding to a weight loss variation of the individual undergoing the extracorporeal blood treatment; a weight loss system configured for actuating the weight loss of the individual during the extracorporeal blood treatment;
wherein the method comprises:
receiving the signal corresponding to the weight loss variation of the individual;
receiving the indicative value of the blood volume variation of the individual;
acquiring a desired value of a parameter of the individual, the parameter of the individual being a function of the ability of the individual to absorb the mass of liquid subtracted from the plasmatic part of the blood by the weight loss system from cells of tissues of the individual; wherein the desired parameter of the individual ($K_{des}$) is defined by a ratio between an initially set weight loss rate ($WLR_0$) and a desired value of a refilling index $IE_{des}$:

$$K_{des} = \left(\frac{WLR_0}{IR_{des}}\right) = \left(\frac{WL_{tot}}{T_{tot} \cdot IR_{des}}\right)$$

where $WL_{tot}$ is total weight loss and $T_{tot}$ is total treatment time;
determining a calculated value of the refilling index ($IR_{CAL}$) as a function of the blood volume variation and a weight loss variation of the individual, wherein the refilling index is defined by function (I) of a ratio between the blood volume variation (ΔBV) and the weight loss variation (ΔWL):

$$IR = f\left(\frac{\Delta BV}{\Delta WL}\right); \quad (I)$$

and controlling the weight loss system on a basis of the desired value of the parameter ($K_{des}$) of the individual and the calculated value of a refilling index ($IR_{cal}$).

23. The method according to claim 22, wherein controlling the weight loss system comprises controlling a weight loss rate for the individual ($WLR_i$) as a function (IV) of the desired value of the parameter of the individual ($K_{des}$) and the calculated value of the refilling index ($IR_{cal}$) according to the following relationship:

$$WLR_i = f(K_{DES}, IR_{CAL}) \quad (IV).$$

24. The method according to claim 22, comprising verifying whether a ratio between the relative variation of blood volume and the variation in weight loss of the individual is in a predetermined relation with the desired parameter of the individual ($K_{des}$).

25. A method of controlling an apparatus for extracorporeal blood treatment, wherein the apparatus comprises a blood treatment device having a blood chamber and a fluid chamber separated from one another by a semipermeable membrane, an extracorporeal blood circuit connected to the blood chamber configured to transport blood from an individual to the blood chamber and to return the blood from the blood chamber to the individual, a blood volume sensor configured to provide a signal corresponding to an indicative value of a blood volume variation of an individual undergoing extracorporeal blood treatment using the apparatus, a sensor configured to emit at least a signal corresponding to a weight loss variation of the individual undergoing the extracorporeal blood treatment; a weight loss system configured for actuating the weight loss of the individual during the extracorporeal blood treatment, and a supply system for supplying a treatment fluid at a predetermined composition to the fluid chamber; wherein the method comprises:

receiving the signal corresponding to the weight loss variation of the individual;

receiving the indicative value of the blood volume variation of the individual;

acquiring a desired value of a refilling index ($IR_{DES}$), the refilling index being a function of the ability of the individual to absorb the mass of liquid subtracted from the plasmatic part of the blood by the weight loss system from cells of tissues of the individual, wherein the refilling index is defined by function (I) of a ratio between the blood volume variation ($\Delta BV$) and the weight loss variation ($\Delta WL$):

$$IR = f\left(\frac{\Delta BV}{\Delta WL}\right) \quad (I)$$

determining a calculated value of the refilling index ($IR_{CAL}$) as a function of the blood volume variation and a weight loss variation of the individual; and controlling the supply system on the basis of the desired value of the refilling index ($IR_{DES}$) and the calculated value of the refilling index ($IR_{CAL}$), wherein controlling the supply system comprises changing the conductivity of the composition or the concentration of at least one substance of the composition on the basis of the desired value of the refilling index and the calculated value of the refilling index.

26. A method of controlling an apparatus for extracorporeal blood treatment, wherein the apparatus comprises a blood treatment device having a blood chamber and a fluid chamber separated from one another by a semipermeable membrane, an extracorporeal blood circuit connected to the blood chamber configured to transport blood from an individual to the blood chamber and to return the blood from the blood chamber to the individual, a blood volume sensor configured to provide a signal corresponding to an indicative value of a blood volume variation of an individual undergoing extracorporeal blood treatment using the apparatus, a sensor configured to emit at least a signal corresponding to a weight loss variation of the individual undergoing the extracorporeal blood treatment; a weight loss system configured for actuating the weight loss of the individual during the extracorporeal blood treatment, and a supply system for supplying a treatment fluid at a predetermined composition to the fluid chamber; wherein the method comprises:

receiving the signal corresponding to the weight loss variation of the individual;

receiving the indicative value of the blood volume variation of the individual;

acquiring a desired value of a parameter of the individual, the parameter of the individual being a function of the ability of the individual to absorb the mass of liquid subtracted from the plasmatic part of the blood by the weight loss system from cells of tissues of the individual; wherein the desired parameter of the individual ($K_{des}$) is defined by a ratio between an initially set weight loss rate ($WLR_0$) and a desired value of a refilling index ($IR_{des}$) as follows:

$$K_{des} = \left(\frac{WLR_0}{IR_{des}}\right) = \left(\frac{WL_{tot}}{T_{tot} \cdot IR_{des}}\right)$$

where $WL_{tot}$ is total weight loss and $T_{tot}$ is total treatment time;

determining a calculated value of the refilling index ($IR_{CAL}$) as a function of the blood volume variation and a weight loss variation of the individual, wherein the refilling index is defined by function (I) of a ratio between the blood volume variation ($\Delta BV$) and the weight loss variation ($\Delta WL$):

$$IR = f\left(\frac{\Delta BV}{\Delta WL}\right), \quad (I)$$

and controlling the supply system on the basis of the desired value of the parameter ($K_{des}$) of the individual and the calculated value of the refilling index ($IR_{CAL}$), and wherein controlling the supply system comprises changing the conductivity of the composition or the concentration of at least one substance of the composition on the basis of the desired value of the refilling index and the calculated value of the refilling index.

* * * * *